(12) United States Patent
Suzuki et al.

(10) Patent No.: US 7,820,835 B2
(45) Date of Patent: Oct. 26, 2010

(54) METHOD FOR PRODUCING FLAVAN DERIVATIVES

(75) Inventors: Keisuke Suzuki, Tokyo (JP); Ken Ohmori, Tokyo (JP); Takashi Higuchi, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 224 days.

(21) Appl. No.: 12/282,293

(22) PCT Filed: Mar. 9, 2007

(86) PCT No.: PCT/JP2007/054669

§ 371 (c)(1),
(2), (4) Date: Sep. 9, 2008

(87) PCT Pub. No.: WO2007/105629

PCT Pub. Date: Sep. 20, 2007

(65) Prior Publication Data

US 2009/0099374 A1    Apr. 16, 2009

(30) Foreign Application Priority Data

Mar. 10, 2006  (JP) .............................. 2006-106895

(51) Int. Cl.
C07D 311/62 (2006.01)
(52) U.S. Cl. .................................................. 549/399
(58) Field of Classification Search .................. 549/399
See application file for complete search history.

(56) References Cited

U.S. PATENT DOCUMENTS 5,180,520 A     1/1993  Wand et al.

FOREIGN PATENT DOCUMENTS

JP          6-501459        2/1994

OTHER PUBLICATIONS

Zaveri, Nurulain, "Synthesis of a 3,4,5-trimethoxybenzoyl ester analogue of epigallocatechin-3-gallate (EGCG): A potential route to the natural product green tea catechin, EGCG", Organic Letters, vol. 3, No. 6, pp. 843-846, 2001.
Makabe, Hidefumi et al., "Synthesis of (4R,15R,16R,21S)- and (4R,15S,16S,21S)-rollicosin", Tetrahedron Letters, vol. 46, pp. 4671-4675, 2005.
Jew, Sang-Sup et al., "Enantioselective synthesis of (2R,3S)- (+)-catechin", Tetrahedron Asymmetry, vol. 13, Issue 7, pp. 715-720, May 2002.
Gu, Wenxin et al., "First enantioselective syntheses of (2R,3R)- and (2S,3S)-3-(4-hydrozxy-3-methoxyphenyl)-2-hydroxymethyl-1,4-benzodioxan-6-carbaldehyde", Tetrahedron Asymmetry, vol. 11, Issue 13, pp. 2801-2807, Jul. 14, 2000.
Higuchi, Takashi et al., "General and convenient approach to flavan-3-ols: stereoselective synthesis of (−)-gallocatechin", Chemistry Letters, 35(9), pp. 1006-1007, particularly schemes 2 to 5, Sep. 2006.

Wan, Sheng Biao et al., "Study of the green tea polyphenols catechin-3-gallate CG) and epicatechin-3-gallate (ECG) as proteasome inhibitors", Bioorganic & Medicinal Chemistry, vol. 12, Issue 13, pp. 3521-3527, Jul. 1, 2004.
Hendrik van Rensburg et al. "Enantioselective Synthesis of the Four Catechin Diastereomer Derivatives", Tetrahedron Letters, vol. 38, No. 17. pp. 3089-3092 (1997).

Primary Examiner—Bernard Dentz
(74) Attorney, Agent, or Firm—Venable LLP; Michael A. Sartori

(57) ABSTRACT

The present invention provides a method for producing flavan derivatives having various substituent groups with controlling the stereochemistry. The method of the present invention includes the steps of: hydratively condensing a phenol compound expressed by formula (I) and an alcohol compound expressed by formula (II) to from an epoxide compound of formula (III); opening the epoxy ring of the epoxide compound of formula (III) to form an iodine-containing compound of formula (IV); and cyclizing the iodine-containing compound to form the flavan derivative of formula (V).

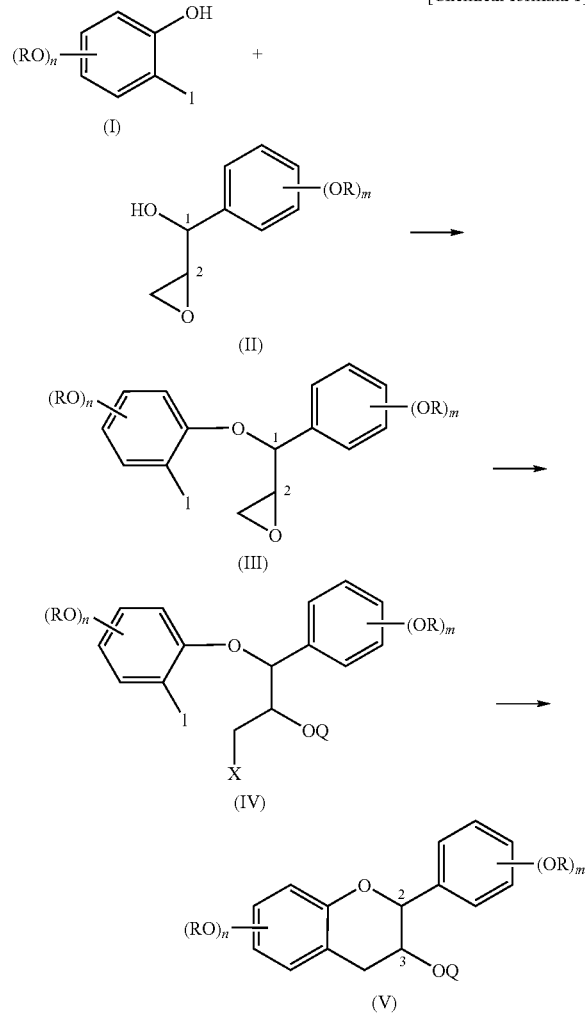

5 Claims, No Drawings

METHOD FOR PRODUCING FLAVAN DERIVATIVES

FIELD OF THE INVENTION

The present invention relates to a method for producing flavan derivatives. In particular, the present invention relates to a method for stereoselectively producing flavan derivatives having various substituent groups.

BACKGROUND ART

In recent years, polyphenols contained in tea and wine have been attracting attention for various physiological activities. Among polyphenols, flavan compounds (for example, catechin) having flavan-3-ol as a mother nucleus structure have been long known as compounds exhibiting strong antioxidant properties. Furthermore, more recently, it has been revealed that flavan compounds have important physiological actions, such as antitumor action, antiviral action, anticavity action, and blood pressure lowering action. Hence, expectation for the application to the field of medicine has been rising.

[Chemical formula 1]

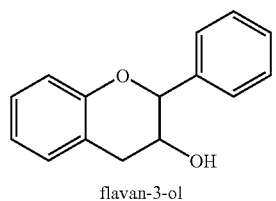

flavan-3-ol

Regarding the biosynthetic pathway of flavan compounds, a theory using chalcone as a precursor as described below is compelling. Based on this, it is considered that involvement of various processes such as oxidation, reduction, rearrangement, and/or isomerization, in combination leads to the formation of a wide variety of analogs having different numbers and binding positions of oxygen functionalities.

[Chemical formula 2]

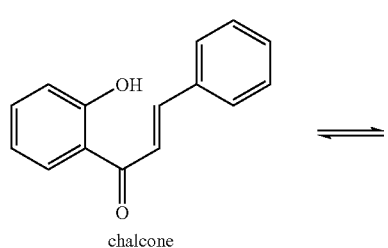

chalcone

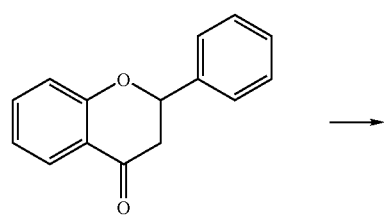

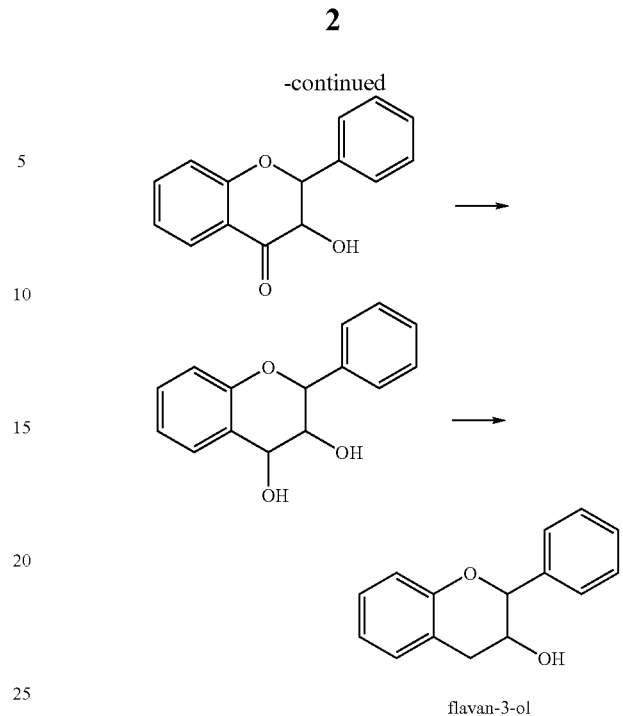

flavan-3-ol

However, due to similarities in the structures of flavan compounds, it is difficult to obtain a single flavan compound from nature by isolation and purification. Against such a background, synthesis of flavan compounds has been actively investigated. Although flavan compounds have relative simple structures, only a few synthesis examples have been reported.

For example, Zaveri et al. reported synthesis of gallocatechin derivatives by simultaneously performing reduction of the carbonyl group in a chalcone derivative and formation of a ring followed by a hydroboration reaction of olefin (refer to Non Patent Document 1). However, this method still has a problem that it is impossible to freely control relative configurations at the 2- and 3-positions, since stereoselectivity in the hydroboration reaction of olefin is determined by the presence of aromatic rings.

[Chemical formula 3]

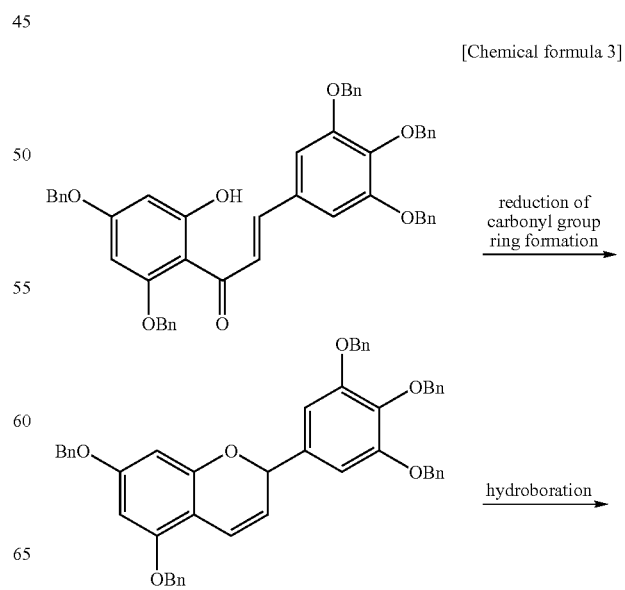

-continued

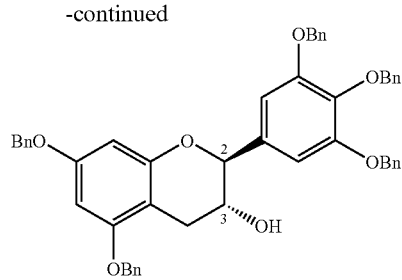

Meanwhile, Ferreira et al. reported synthesis of flavan derivatives by asymmetric dihydroxylation of (E)-olefin derivative derived from chalcone to introduce a chiral center corresponding to the 3-position of a flavan derivative, followed by dehydrative cyclization reaction under acidic condition (refer to Non Patent Document 2). However, this method has a problem regarding stereochemical control. More specifically, this method does not have high stereoselectivity in the dehydrative cyclization reaction, and thereby provides two kinds of diastereomer.

[Chemical formula 4]

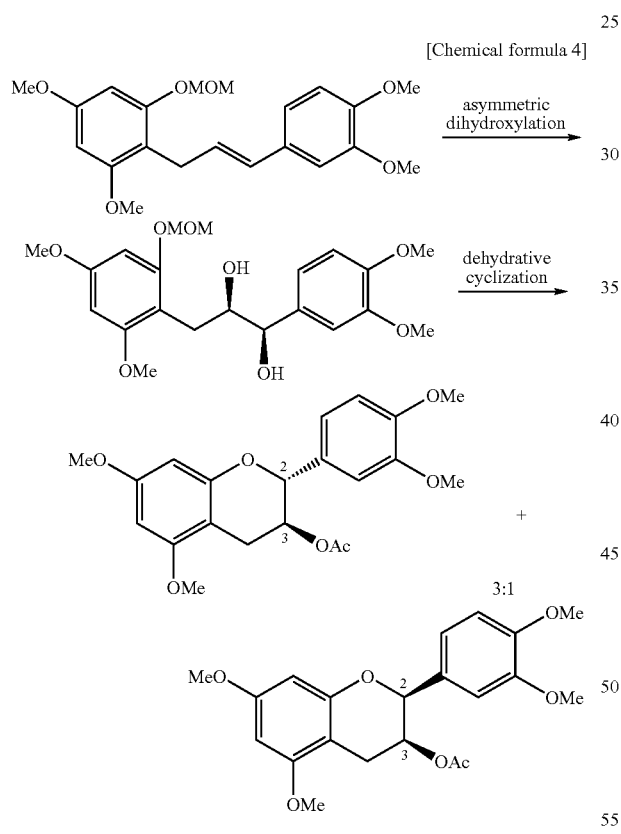

Furthermore, Hyeung-Geun Park et al. reported stereoselective synthesis of flavan derivatives by using caffeic acid and a phloroglucinol derivative (refer to Non Patent Document 3). In this method, an aldehydes body obtained from caffeic acid going through several steps, such as asymmetric dihydroxylation, is coupled with a lithiated phloroglucinol derivative to give an intermediate having a necessary carbon backbone. Then, after being subjected to further conversion, the obtained intermediate forms a pyran ring by the Mitsunobu reaction, and a flavan derivative is obtained. Although a flavan derivative having a desired stereochemistry can be obtained by this method, there is a problem in yields of the key reactions, the coupling reaction with a phloroglucinol derivative and the pyran ring formation by the Mitsunobu reaction. Therefore, this method is hardly an effective method.

[Chemical formula 5]

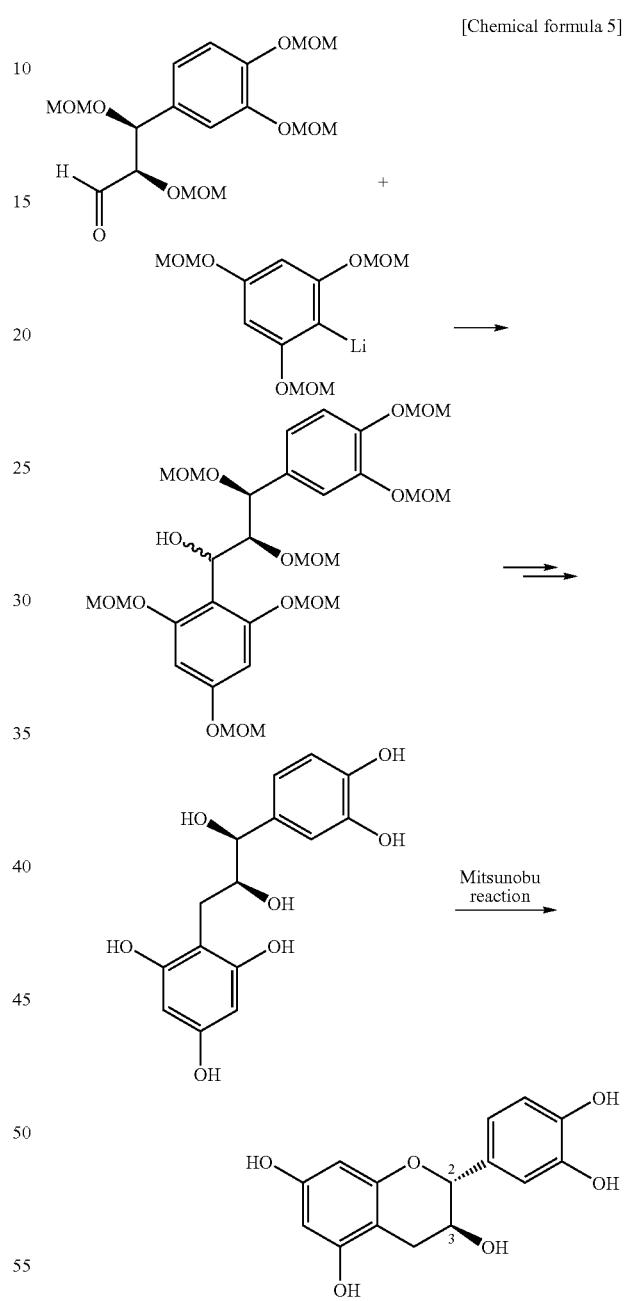

[Non Patent Document 1] Zaveri et al., Organic Letters, 3, pp. 843-846 (2001)

[Non Patent Document 2] Ferreira et al., Tetrahedron Letters, 38, 3089-3092 (1997)

[Non Patent Document 3] Hyeung-Geun Park et al., Tetrahedron Asymmetry, 13, 715-720 (2002)

[Non Patent Document 4] Zu et al., Tetrahedron Asymmetry, 11, pp. 2801-2809 (2000)

DISCLOSURE OF THE INVENTION

An object of the present invention is to provide a method for producing flavan derivatives having various substituent groups efficiently while controlling their stereochemistries.

A method for producing flavan derivatives of the present invention is characterized by including the steps of:

(1) dehydratively condensing a phenol compound of formula (I) and an alcohol compound of formula (II) to obtain an epoxide compound of formula (III),

[Chemical formula 6]

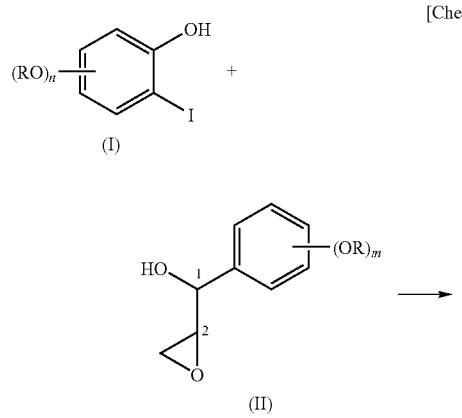

(wherein:
R represents, in each of the appearances, H; an allyl group; or an alkyl group, an aryl group or an arylalkyl group which may be substituted by an alkoxy group, an alkylthio group, an acyloxy group, or an alkoxycarbonyl group;
n represents an integer from 0 to 4; and
m represents an integer from 0 to 5);

(2) opening the epoxy ring of the epoxide compound of formula (III) to obtain an iodine-containing compound of formula (IV),

[Chemical formula 7]

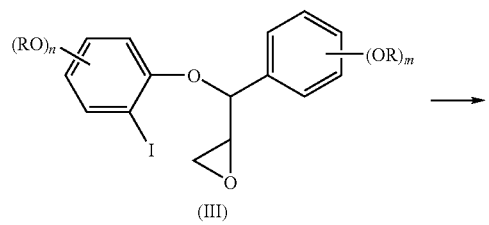

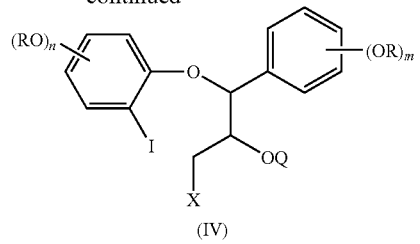

(wherein:
R represents, in each of the appearances, H; an allyl group; or an alkyl group, an aryl group or an arylalkyl group which may be substituted by an alkoxy group, an alkylthio group, an acyloxy group, or an alkoxycarbonyl group;
n represents an integer from 0 to 4;
m represents an integer from 0 to 5;
X represents a halogen, an alkylsulfonyloxy group, or an arylsulfonyloxy group; and
Q represents H; a silyl group; or an alkyl group, an aryl group or an arylalkyl group which may be substituted by an alkoxy group, an alkylthio group, an acyloxy group or an alkoxycarbonyl group);

(3) cyclizing the iodine-containing compound of formula (IV) to obtain a flavan derivative of formula (V),

[Chemical formula 8]

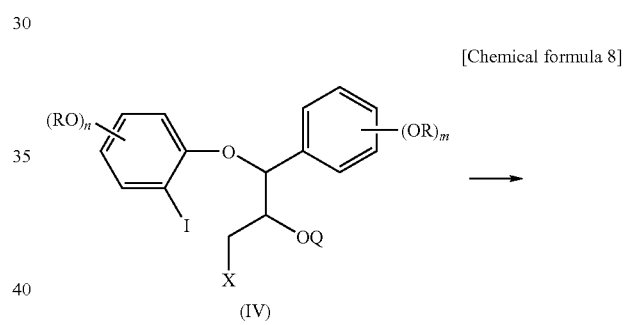

(wherein:
R represents, in each of the appearances, H; an allyl group; or an alkyl group, an aryl group or an arylalkyl group which may be substituted by an alkoxy group, an alkylthio group, an acyloxy group or an alkoxycarbonyl group;
n represents an integer from 0 to 4;
m represents an integer from 0 to 5; and
Q represents H; a silyl group; or an alkyl group, an aryl group or an arylalkyl group which may be substituted by an alkoxy group, an alkylthio group, an acyloxy group, or an alkoxycarbonyl group).

Here, a flavan derivative of formula (V) in which the 2-position has (S) or (R) configuration, respectively, can be obtained, by using an alcohol compounds of formula (II) in which the 1-position has (R) or (S) configuration. Furthermore, a flavan derivative of formula (V) in which the 3-position has (R) or (S) configuration, respectively, can be obtained, by using an alcohol compound of formula (II) in which the 2-position has (R) or (S) configuration.

The production method of the present invention adopting the above-described configuration enables efficient production of flavan derivatives having various substituent groups and stereochemistries. Moreover, ther production method of the present invention exhibits high stereoselectivity, and enables control over stereochemistry of the resultant flavan derivative of formula (V) by controlling the stereochemistries of the 1- and 2-positions in an alcohol compound of formula (II) used as a starting material. The resultant flavan derivatives are expected to have various physiological functions, and they are useful as pharmaceutical products, health food products, cosmetic products, and their precursors.

BEST MODE FOR CARRYING OUT THE INVENTION

Different from the methods reported in Non Patent Document 1 to 3 in which cyclization for forming a carbon-oxygen bond is performed after all the essential carbon-carbon bonds have been formed, the method for producing flavan derivatives of the present invention is a method in which a carbon-oxygen bond is formed in the initial stage, and then cyclization for forming a carbon-carbon bond is performed. More specifically, the method for producing flavan derivatives of the present invention includes the steps of:

(1) dehydratively condensing a phenol compound expressed by formula (I) and an alcohol compound expressed by formula (II) to obtain an epoxide compound of formula (III);

(2) opening the epoxy ring of the epoxide compound of formula (III) to obtain an iodine-containing compound of formula (IV);

(3) cyclizing the iodine-containing compound of formula (IV) to obtain a flavan derivative of formula (V).

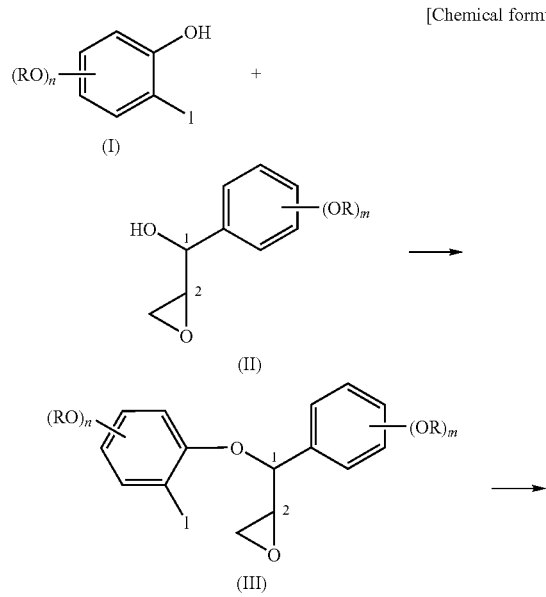

[Chemical formula 9]

In the formulas, n represents an integer in a range from 0 to 4, and m represents an integer in a range from 0 to 5.

Here, R represents, in each of the appearances, H; an allyl group; or an alkyl group, an aryl group, or an arylalkyl group which may be substituted by an alkoxy group, an alkylthio group, an acyloxy group, or an alkoxycarbonyl group. In the case where multiple R exist, they may be the same or different from each other. In the present invention, an alkyl group which may be substituted by an alkoxy group, an alkylthio group, an acyloxy group, or an alkoxycarbonyl group includes: a methyl group; an ethyl group; a propyl group; a butyl group; a hexyl group; an octyl group; a methoxymethyl group; an ethoxymethyl group; an ethoxyethyl group; a methylthiomethyl group; a methylthioethyl group; an acetoxymethyl group; an acetoxyethyl group; an acetoxybutyl group; a methoxycarbonylmethyl group; a methoxycarbonylethyl group; an ethoxycarbonylmethyl group; an ethoxycarbonylethyl group; and their isomers and the like. In the present invention, an aryl group which may be substituted by an alkoxy group, an alkylthio group, an acyloxy group, or an alkoxycarbonyl group includes: a phenyl group; a naphthyl group; an anthryl group; a phenanthryl group; a fluorenyl group; a methoxyphenyl group; an ethoxyphenyl group; a methylthiophenyl group; an ethylthiophenyl group; an acetoxyphenyl group; a methoxycarbonylphenyl group; an ethoxycarbonylphenyl group; and their isomers and the like. In the present invention, an arylalkyl group which may be substituted by an alkoxy group, an alkylthio group, an acyloxy group, or an alkoxycarbonyl group includes: a benzyl group; a phenylethyl group; a phenylpropyl group; a methoxyphenylmethyl (anisyl) group; an ethoxyphenylmethyl group; a methylthiophenylmethyl group; an ethylthiophenylmethyl group; an acetoxyphenylmethyl group; a methoxycarbonylphenylmethyl group; an ethoxycarbonylphenylmethyl group; and their isomers and the like.

In the formulas, X represents a halogen, an alkylsulfonyloxy group, or an arylsulfonyloxy group. A useful halogen includes F, Cl, Br and I, and Cl and Br are more preferable. A useful alkylsulfonyloxy group includes a methanesulfonyloxy group, an ethanesulfonyloxy group, a propanesulfonyloxy group, a trifluoromethanesulfonyloxy group and the like. A useful arylsulfonyloxy group includes a benzenesulfonyloxy group, a toluenesulfonyloxy group, a naphthalenesulfonyloxy group and the like.

In the formulas, Q represents H; a silyl group; or an alkyl group, an aryl group, or an arylalkyl group, which may be substituted by an alkoxy group, an alkylthio group, an acyloxy group, or an alkoxycarbonyl group. A silyl group which can be used includes: a trimethylsilyl group; a triethylsilyl group; a tri-n-propylsilyl group; a triisopropylsilyl group; a tri-n-butylsilyl group; t-butyldimethylsilyl group; a t-butyldiphenylsilyl group; a triphenylsilyl group; a tribenzylsilyl group; and the like. A useful alkyl group which may be substituted by an alkoxy group, an alkylthio group, an acyl group, an acyloxy group, or an alkoxycarbonyl group includes: a methyl group; an ethyl group; a propyl group; butyl group; a hexyl group; an octyl group; a methoxymethyl group; an ethoxymethyl group; an ethoxyethyl group; a methylthiomethyl group; a methylthioethyl group; an acetoxymethyl group; an acetoxyethyl group; an acetoxybutyl group; a methoxycarbonylmethyl group; a methoxycarbonylethyl group; an ethoxycarbonylmethyl group; an ethoxycarbonylethyl group; and their isomers and the like. A useful aryl group which may be substituted by an alkoxy group, an alkylthio group, an acyloxy group, or an alkoxycarbonyl group includes: a phenyl group; a naphthyl group; an anthryl group; a phenanthryl group; a fluorenyl group; a methoxyphenyl group; an ethoxyphenyl group; a methylthiophenyl group; an ethylthiophenyl group; an acetoxyphenyl group; a methoxycarbonylphenyl group; an ethoxycarbonylphenyl group; and their isomers and the like. A useful arylalkyl group which may be substituted by an alkoxy group, an alkylthio group, an acyloxy group, or an alkoxycarbonyl group includes: a benzyl group; a phenylethyl group; a phenylpropyl group; methoxyphenylmethyl (anisyl) group; an ethoxyphenylmethyl group; a methylthiophenylmethyl group; an ethylthiophenylmethyl group; an acetoxyphenylmethyl group; a methoxycarbonylphenylmethyl group; an ethoxycarbonylphenylmethyl group; and their isomers and the like.

An method for producing flavan derivatives of the present invention enables stereospecific production of a flavan derivative of formula (V) by using an alcohol compound of formula (II) having a predetermined stereochemistry. For example, as shown below, a flavan derivative expressed by formula (Va) having (2S,3R) configuration can be obtained by using an alcohol compound expressed by formula (IIa) having (1R, 2R) configuration. Therefore, according to the method of the present invention, a flavan derivative of formula (V) having a predetermined configuration can be obtained by using an alcohol compound of formula (II) having a specific configuration.

[Chemical formula 10]

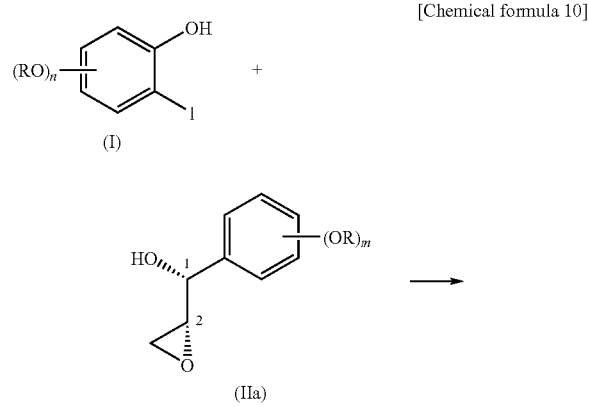

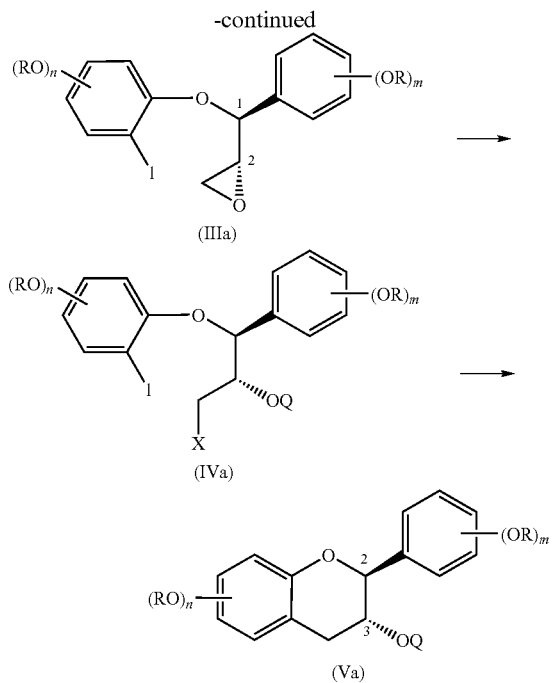

The first step (1) of the method for producing flavan derivatives of the present invention is a step of dehydratively condensing a phenol compound of formula (I) and an alcohol compound of formula (II) to obtain an epoxide compound of formula (III).

[Chemical formula 11]

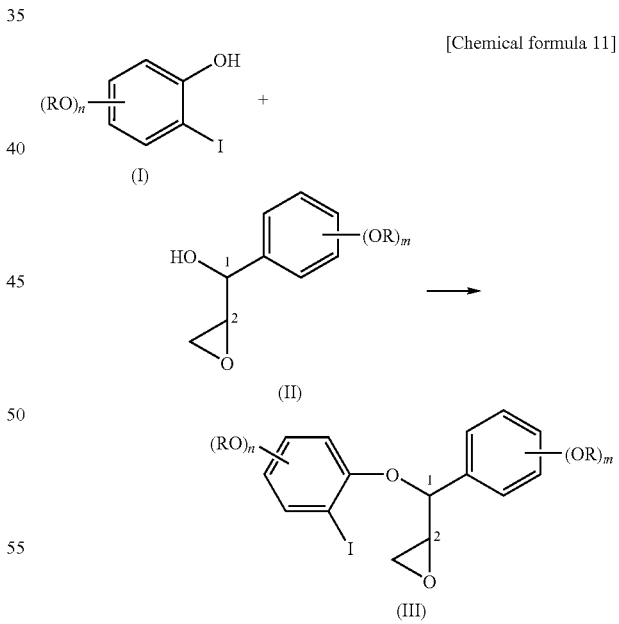

The phenol compound of formula (I) can be prepared by any method known in the art using a commercially-available phenol compound. Meanwhile, the alcohol compound of formula (II) can be stereoselectively prepared from a benzaldehyde derivative in accordance with the method by Gu et al., for example (refer to Non Patent Document 4). Here, in the case of intending to obtain a flavan derivative (V) of R=H at the end, it is preferable to use compounds respectively of formula (I) and formula (II) having a protection group (for example, R=benzyl group) which allows deprotection under mild conditions.

The step (1) may be performed by reacting a phenol compound of formula (I) and an alcohol compound of formula (II) in the presence of an acid catalyst. Alternatively, the step (1) may be performed by sulfonylating the hydroxyl group at the 1-position of an alcohol compound of formula (II) and then reacting with a phenol compound of formula (I) under basic conditions. Sulfonylation can be performed by using a sulfonylhalide, such as methanesulfonylchloride. As for the base, any compound, such as potassium carbonate and sodium carbonate, which is known in the art can be used.

As an alternative method, the step (1) can be carried out by reacting both of the compounds in the presence of an azo compound and a phosphine, so-called the Mitsunobu reaction. A useful azo compound includes diethyl azocarboxylate (DEAD), N,N,N',N'-tetramethyl azodicarboxamide, and the like. Here, a useful phosphine includes triphenylphosphine, tributylphosphine and the like. The step (1) can be carried out by stirring the compounds respectively of formula (I) and formula (II), the azo compound and the phosphine in an inert solvent (hexane, benzene, toluene, or the like) at a temperature in a range from 0 to 30° C.

In the present invention, the step (1) is desirably carried out by the Mitsunobu reaction, since the compound of formula (III) having the defined stereochemistry at the 1-position can be obtained in high yield.

The second step (2) of the method for producing flavan derivatives of the present invention is a step of opening the epoxy ring of the epoxide compound of formula (III) to obtain an iodine-containing compound of formula (IV).

[Chemical formula 12]

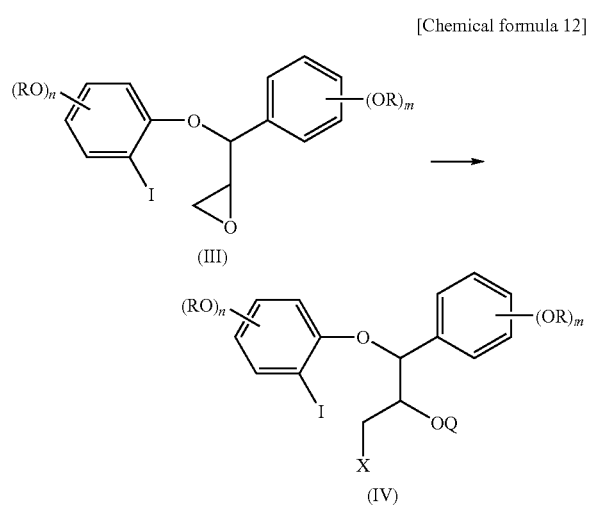

The step (2) can be carried out by treating the epoxide compound with a nucleophilic agent in the presence of a protonic acid or a Lewis acid. By using a metal halide, such as LiCl, LiBr, and LiI, as the nucleophilic agent, a compound (IV) in which X is halogen can be obtained. Here, the step (2) may be carried out by using a reactant, such as $Li_2NiBr_4$ (which can be prepared from LiBr and $NiBr_2$) which functions as both a nucleophilic agent and a Lewis acid.

Alternatively, a compound (IV) in which X is alkylsulfonyloxy group or X is arylsulfonyloxy group can be obtained by preparing a compound (IV) in which X is OH using water as a nucleophilic agent and then selectively sulfonylating only a primary hydroxyl group. The selective sulfonylation of a primary hydroxyl group can be achieved by any method known in the art.

The ring opening of an epoxy group in the step (2) can be desirably carried out in a solution of ether-based solvents (tetrahydrofuran, 1,2-dimethoxyethane, glymes and the like), halogen-containing hydrocarbon solvents (dichloromethane, chloroform, 1,2-dichloromethane, and the like), or aprotic polar solvents (N,N-dimethylformamide, N,N-dimethylacetoamide, dimethylsufoxide, and the like), at a temperature in a range from 0 to 30° C.

In carrying out the following step (3), it is desirable to protect a secondary hydroxyl group (Q=H) formed by the ring opening of the epoxy group by various methods. For example, a compound (IV) in which Q=silyl group can be obtained by treatment with various silylation agents in the presence of a weak base. Alternatively, by adopting any method known in the art, an alkyl group, an aryl group, or an arylalkyl group, which may include a substituent group, can be introduced as Q.

The third step (3) of the method for producing flavan derivatives of the present invention is a step of cyclizing the iodine-containing compound of formula (IV) to obtain a flavan derivative of formula (V).

[Chemical formula 13]

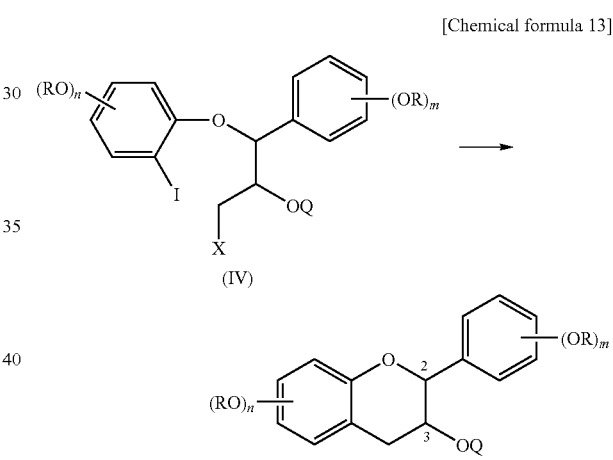

The step (3) can be carried out by treating the iodine-containing compound of formula (IV) with an organometallic compound. A useful organometallic compound includes: organic Li compounds, organic Mg compounds, organic Li—Mg compounds, organic copper compounds, or the like; preferably organic Li compounds, organic Mg compounds, or organic Li—Mg compounds; and more preferably organic Li—Mg compounds. Methyl lithium, ethyl lithium, butyl lithium (including isomers), phenyl lithium, and the like can be used as the organic Li compound. Methyl magnesium bromide, methyl magnesium chloride, methyl magnesium iodide, butyl magnesium bromide (including isomers), butyl magnesium chloride (including isomers), butyl magnesium iodide (including isomers), phenyl magnesium bromide, phenyl magnesium chloride, phenyl magnesium iodide, and the like can be used as the organic Mg compound. In the meantime, lithium trimethylmagnesate prepared from methyl magnesium bromide and methyllithium ($Me_3MgLi$), lithium tributylmagnesate ($Bu_3MgLi$) prepared from butyl magnesium bromide and butyl lithium, lithium triphenylmagnesate ($Ph_3MgLi$) prepared from phenyl magnesium bromide and phenyl lithium, and the like can be used as the organic Li—Mg compound prepared by the organic Li compound and the organic Mg compound, for example. As an alternative method, iodine may be eventually converted to copper by treating the iodine compound of formula (IV) with the organic Li compound or the organic Mg compound to exchange iodine with a metal (Li or Mg), and then treating it with a copper compound (CuCN, CuBr, CuI or the like).

The step (3) can be carried out by treating a solution of the iodine compound of formula (IV) in an ether-based solvent (tetrahydrofuran, diethyl ether, 1,2-dimethoxyethane, or the like) with the organic metal compound at a temperature in a range from −100 to −70° C. Here, the iodine-metal exchange may be promoted by mixing an aprotic polar solvent (hexamethyl phosphoramide (HMPA), 1,3-dimethyl-3,4,5,6-tetrahydro-2(1H)-pyrimidinone (DMPU), or the like) into the solution. In the meantime, if necessary, the cyclization reaction may be promoted by raising the temperature of the reaction mixture (for example, up to 0° C.) after addition of the organic metal compound.

Furthermore, substituent groups in the obtained flavan derivative of formula (V) can be modified by any method known in the art. For example, a flavan derivative of formula (V) in which Q is H can be obtained by treating a flavan derivative of formula (V) in which Q is silyl group with fluoride ion or an acid to remove a silyl group. Meanwhile, a flavan derivative of formula (V) in which R is H can be obtained by hydrogenolysis of a flavan derivative of formula (V) in which R is benzyl group.

EXAMPLE 1

Synthesis of an Epoxy Compound (III-1)

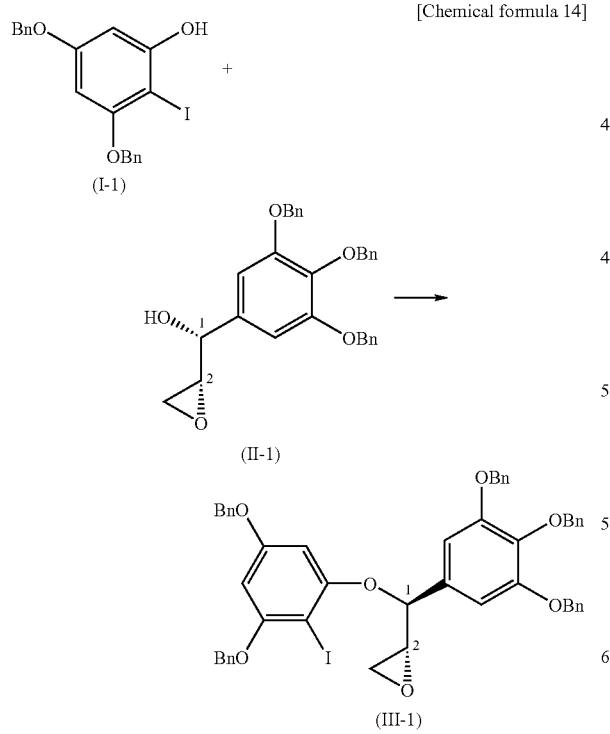

Under argon atmosphere, into a reaction mixture which was prepared by dissolving 470 mg (1.00 mmol) of an alcohol compound (II-1), 518 mg (3.00 mmol) of N,N,N′,N′-tetramethyl azodicarboxamide, and 1.30 g (3.00 mmol) of a phenol compound (I-1) into 10 mL of toluene and then cooled down to 0° C., 3.01 mL (3.00 mmol) of a toluene solution of tributylphosphine was added dropwise and stirred at 0° C. After stirring overnight, the reaction was quenched by adding water, and the aqueous layer was extracted with ethyl acetate three times. The obtained organic layer was washed with a saturated saline solution, dried over anhydrous magnesium sulfate, and filtered. Then, the solvent was removed by evaporation under reduced pressure, and the residue was purified by silica gel chromatography (n-hexane:toluene:ethyl acetate=8:8:1), and thin-layer chromatography (n-hexane:toluene:ethyl acetate=4:4:1). Consequently, 823 mg (yield 93.0%) of an epoxy compound (III-1) was obtained as a colorless viscous material.

$^1$H NMR (400 MHz, CDCl$_3$) δ 2.77 (dd, 1H, J=5.6, 4.4 Hz), 3.05 (dd, 1H, J=5.6, 2.4 Hz), 3.23 (ddd, 1H, J=4.4, 3.6, 2.4 Hz), 4.84 (s, 2H), 5.00-5.13 (m, 8H), 5.06 (d, 1H, J=3.6 Hz), 6.02 (d, 1H, J=2.4 Hz), 6.21 (d, 1H, J=2.4 Hz) 6.71 (s, 2H), 7.24-7.56 (m, 25H);

IR (neat) 3900, 3630, 3150, 3075, 3050, 3020, 2970, 2920, 2860, 2730, 2240, 2070, 1945, 1870, 1800, 1740, 1580, 1500, 1430, 1420, 1370, 1330, 1220, 1160, 1100, 1020, 900, 840, 800, 730, 690, 640, 620 cm$^{-1}$;

$[\alpha]_D^{27}$ −35 (c 0.54, CHCl$_3$);

Elementary Analysis

Calculated (C$_{50}$H$_{43}$BrIO$_7$): C, 68.03; H, 4.91.

Found: C, 68.33; H, 4.97.

Synthesis of an Iodine-Containing Compound (VI-1a) Having a Free Hydroxyl Group

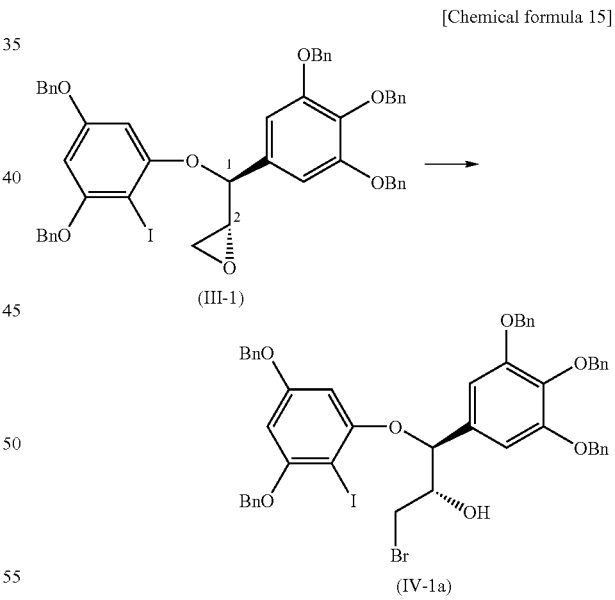

Under argon atmosphere, into a reaction mixture which was prepared by dissolving 288 mg (0.326 mmol) of the epoxy compound (III-1) into 3.3 mL of tetrahydrofuran and then cooled down to 0° C., 1.30 mL (0.521 mmol) of a tetrahydrofuran solution of Li$_2$NiBr$_4$ was added dropwise and stirred at 0° C. After 6 hours, 0.160 mL (0.065 mmol) of the tetrahydrofuran solution of Li$_2$NiBr$_4$ was again added dropwise thereinto, and further stirred at 0° C. for 2 hours. Then, the reaction was quenched with a phosphate buffer, and the aqueous layer was extracted with ethyl acetate three times.

The obtained organic layer was washed with a saturated saline solution, dried over anhydrous magnesium sulfate, and filtered. Then, the solvent was removed by evaporation under reduced pressure. The residue was purified by silica gel chromatography (n-hexane:toluene:ethyl acetate=4:4:1), and thin-layer chromatography (n-hexane:toluene:ethyl acetate=4:4:1). Consequently, 291 mg (yield 92.7%) of an iodine-containing compound (VI-1a) having a free hydroxyl group was obtained as a colorless needle-like crystal.

$^1$H NMR (400 MHz, CDCl$_3$) δ 2.33 (d, 1H, J=6.0 Hz), 3.45 (dd, 1H, J=10.8, 3.6 Hz), 3.70 (dd, 1H, J=10.8, 6.8 Hz), 4.04 (ddd, 1H, J=6.8, 6.0, 5.6, 3.6 Hz), 4.80 (dd, 2H, J=16.4, 12.0 Hz), 5.00-5.10 (m, 8H), 5.11 (d, 1H, J=5.6 Hz), 5.94 (d, 1H, J=2.0 Hz), 6.21 (d, 1H, J=2.0 Hz), 6.63 (s, 2H), 7.24-7.52 (m, 25H);

IR (neat) 3480, 3070, 3050, 3020, 2920, 2890, 2860, 2240, 1940, 1870, 1800, 1570, 1490, 1450, 1420, 1365, 1325, 1220, 1160, 1105, 1070, 1020, 1010, 980, 905, 805, 730, 695 cm$^{-1}$;

$[α]_D^{28}$ −68.3 (c 1.08, CHCl$_3$);

Elementary Analysis
Calculated (C$_{50}$H$_{44}$BrIO$_7$): C, 62.32; H, 4.60.
Found: C, 62.55; H, 4.67.

Synthesis of an Iodine-Containing Compound (VI-1b) Having TBS Ether

[Chemical formula 16]

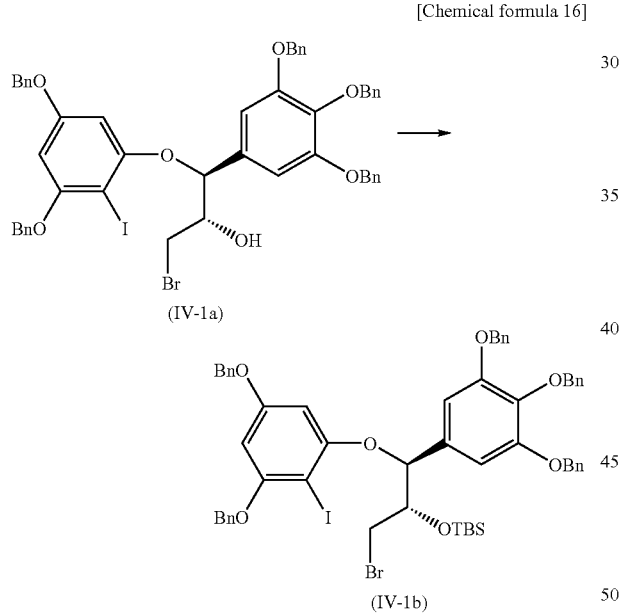

Under argon atmosphere, into a reaction mixture which was prepared by dissolving 552 mg (0.573 mmol) of the iodine-containing compound (VI-1a) having a free hydroxyl group and 215 mg (2.01 mmol) of 2,6-di-tert-butylpyridine into 6.0 mL of dichloromethane and then cooled down to 0° C., 227 mg (0.573 mmol) of tert-butyldiemthylsilyl triflate was added dropwise and stirred at 0° C. for 1 hour. To the reaction mixture, a sodium carbohydrate solution was added to quench the reaction, and the aqueous layer was extracted with ethyl acetate three time. The obtained organic layer was washed with a saturated saline solution, dried over anhydrous magnesium sulfate, and filtered. Then, the solvent was removed by evaporation under reduced pressure. The residue was purified by silica gel chromatography (n-hexane:ethyl acetate=8:1). Consequently, 575 mg (yield 93.0%) of an iodine-containing compound (VI-1b) having tert-butyldimethylsilyl (TBS) ether was obtained as a colorless viscous material.

$^1$H NMR (400 MHz, CDCl$_3$) δ −0.42 (s, 3H), −0.05 (s, 3H), 0.82 (s, 9H), 3.48 (dd, J=10.8, 3.6 Hz), 3.98 (ddd, 1H, J=4.4, 3.6, 2.8 Hz), 4.09 (dd, 1H, J=10.8, 2.8 Hz), 4.82 (dd, 2H, J=23.6, 11.2 Hz), 5.08 (d, 1H, J=6.8 Hz) 5.02-5.12 (m, 8H), 6.06 (d, 1H, J=2.4 Hz), 6.20 (d, 1H, J=2.4 Hz), 6.73 (s, 1H), 7.13-7.58 (m, 25H);

IR (neat) 3070, 3050, 3010, 2940, 2915, 2870, 2845, 2230, 1940, 1860, 1800, 1580, 1490, 1450, 1420, 1365, 1320, 1250, 1220, 1180, 1160, 1110, 1070, 1020, 1010, 980, 950, 900, 835, 820, 805, 775, 730, 690, 665, 650, 620 cm$^{-1}$;

$[α]_D^{32}$ −76 (c 0.31, CHCl$_3$);

Elementary Analysis
Calculated (C$_{56}$H$_{58}$BrIO$_7$Si): C, 62.40; H, 5.42.
Found: C, 62.20; H, 5.53.

Synthesis of a Benzyl and TBS Protected Form of (−)-Gallocatechin

[Chemical formula 17]

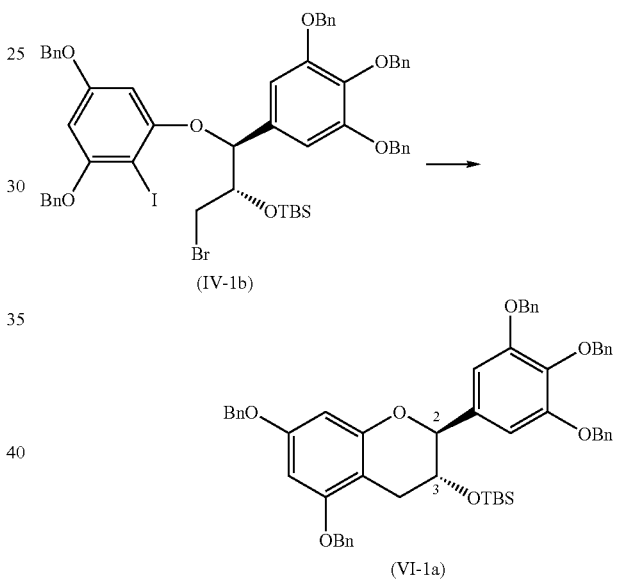

Under argon atmosphere, into a reaction mixture which was prepared by adding 38.2 mg (0.213 mmol) of HMPA and 0.049 mL mmol) of phenylmagnesium bromide into 1.0 mL of tetrahydrofuran and then cooled down to 0° C., 0.102 mL (0.107 mmol) of phenyl lithium was added dropwise and stirred at 0° C. for 30 minutes. The reaction mixture was cooled down to −78° C. Into the reaction mixture, a tetrahydrofuran solution (0.5 ml) containing 23.0 mg (0.213 mmol) of an iodine-containing compound (VI-1b) having TBS ether was added dropwise and stirred at −78° C. for 1 hour. The temperature of the reaction mixture was raised to 0° C., and then further stirred for 10 minutes. Thereafter, the reaction was quenched by adding methanol-D (CH$_3$OD), and an ammonium chloride solution was added thereto. The aqueous layer was extracted with n-hexane three times, and the obtained organic layer was washed with a saturated saline solution. The obtained organic layer was dried over anhydrous magnesium sulfate, and filtered. Then, the solvent was removed by evaporation under reduced pressure. The residue was purified by thin-layer chromatography (n-hexane:toluene:ethyl acetate=16:16:1). Consequently, 17.9 mg (yield 96.4%) of a benzyl and TBS protected form of (−)-gallocatechin was obtained as a colorless viscous material.

$^1$H NMR (400 MHz, CDCl$_3$) δ −0.41 (s, 3H), 0.12 (s, 3H), 0.75 (s, 9H), 2.63 (dd, 1H, J=16.4, 9.2 Hz), 3.12 (dd, 1H, J=16.4, 6.0 Hz), 3.91 (ddd, 1H, J=9.2, 8.4, 6.0 Hz), 4.55 (d, 1H, J=8.4 Hz) 4.9-5.16 (m, 10H), 6.22 (d, 1H, J=1.2 Hz), 6.25 (d, 1H, J=1.2 Hz), 6.78 (s, 2H), 7.26-7.52 (m, 25H);

IR (neat) 3070, 3050, 3020, 2935, 2920, 2860, 2840, 2230, 1940, 1870, 1800, 1740, 1610, 1585, 1495, 1450, 1430, 1370, 1325, 1245, 1180, 1170, 1140, 1120, 1050, 1025, 1000, 935, 900, 880, 870, 830, 805, 775, 730, 690, 675, 660 cm$^{-1}$;

$[α]_D^{27}$ −12.8 (c 1.33, CHCl$_3$);

Elementary Analysis

Calculated (C$_{56}$H$_{58}$O$_7$Si): C, 77.21; H, 6.71.

Found: C, 77.41; H, 6.96.

Synthesis of a Benzyl Protected Form of (−)-Gallocatechin

[Chemical formula 18]

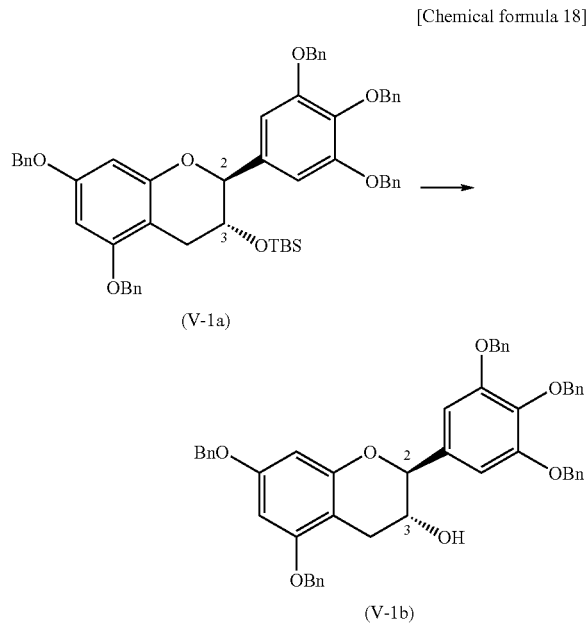

Under argon atmosphere, into a reaction mixture which was prepared by dissolving 81.0 mg (0.930 mmol) of the benzyl and TBS protected form of (−)-gallocatechin (V-1a) into 1.5 mL of tetrahydrofuran and then cooled down to 0° C., 0.121 mL (0.121 mmol) of tetrabutylammonium fluoride was added dropwise and stirred at 0° C. After 3 hours, 0.019 mL (0.019 mmol) of tetrabutylammonium fluoride was further added dropwise thereinto and stirred at 0° C. Thereafter, the reaction was quenched by adding a phosphate buffer. The aqueous layer was extracted with ethyl acetate three times. The obtained organic layer was washed with a saturated saline solution, dried over anhydrous magnesium sulfate, and filtered. Then, the solvent was removed by evaporation under reduced pressure. The residue was purified by silica gel chromatography (n-hexane:ethyl acetate=2:1). Consequently, 61.4 mg (yield 87.2%) of a benzyl protected form of (−)-gallocatechin (V-1b) was obtained as a colorless crystal.

$^1$H NMR (400 MHz, CDCl$_3$) δ 1.58 (d, 1H, J=3.6 Hz), 2.64 (dd, 1H, J=16.4, 8.8 Hz), 3.11 (dd, 1H, J=16.4, 5.6 Hz), 3.97 (dddd, 1H, J=8.8, 8.0, 5.6, 3.6 Hz), 4.60 (d, 1H, J=8.0 Hz) 4.98-5.15 (m, 10H), 6.22 (d, 1H, J=2.4 Hz), 6.28 (d, 1H, J=2.4 Hz), 6.73 (s, 2H), 7.22-7.44 (m, 25H);

IR (neat) 3550, 3450, 3075, 3040, 3015, 2900, 2860, 2230, 1940, 1860, 1800, 1610, 1580, 1490, 1430, 1370, 1210, 1140, 1110, 1045, 1020, 900, 810, 730, 690 cm$^{-1}$;

$[α]_D^{27}$ +9.7 (c 0.35, CHCl$_3$);

Elementary Analysis

Calculated (C$_{50}$H$_{44}$O$_7$): C, 79.34; H, 5.86.

Found: C, 79.55; H, 6.09.

Synthesis of (−)-Gallocatechin (V-1c)

[Chemical formula 19]

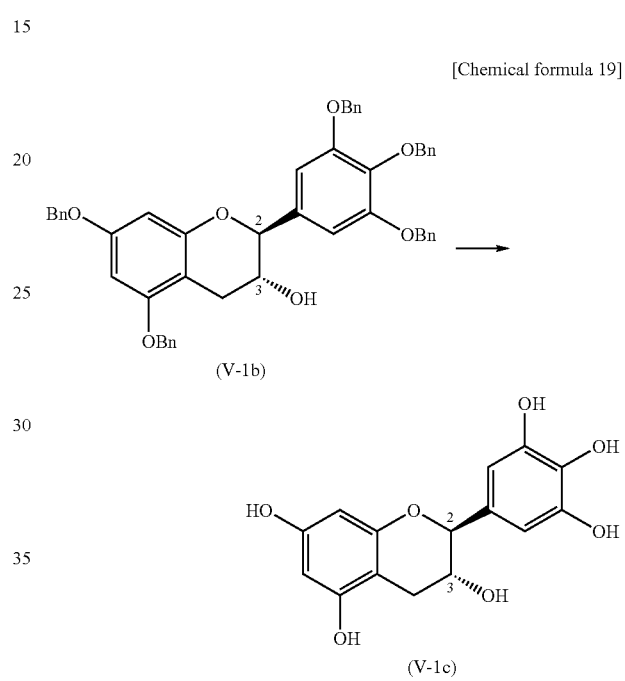

19.0 mg (0.025 mmol) of the benzyl protected form of (−)-gallocatechin (V-1b) was dissolved into 2.0 mL of tetrahydrofuran, 2.0 mL of methanol, and 0.5 mL of water. Then 4.6 mg of palladium hydroxide was added thereto, and stirred at room temperature under hydrogen atmosphere. After 5 hours, under argon gas atmosphere, the mixture was filtrated through a celite pad, and then the filtrate was treated by gel filtration column chromatography Sephadex (trademark) LH-20 (eluate:methanol). After adding water to the obtained solution of a target substance, the solution was concentrated under reduced pressure to remove contained methanol. The residue was freeze-dried, and then 10.5 mg of hydrated (−)-gallocatechin (V-1c) was obtained as a freeze-dried material.

$^1$H NMR (400 MHz, CD$_3$OD) δ 2.49 (dd, 1H, J=16.0, 8.0 Hz), 2.80 (dd, 1H, J=16.0, 5.2 Hz), 3.95 (ddd, 1H, J=8.0, 7.2, 5.2 Hz), 4.51 (d, 1H, J=7.2 Hz), 5.85 (d, 1H, J=2.0 Hz), 5.91 (d, 1H, J=2.8 Hz), 6.39 (s, 2H);

$[α]_D^{25}$ −12 (c 0.10, acetone/H$_2$O, 1/1 v/v);

HRMS (FAB, m-nitrobenzyl alcohol)

Calculated C$_{15}$H$_{15}$O$_7$ ([M+H]$^+$): m/z: 307.0818.

Found: m/z: 307.0839.

EXAMPLE 2

Synthesis of an Epoxy Compound (III-2)

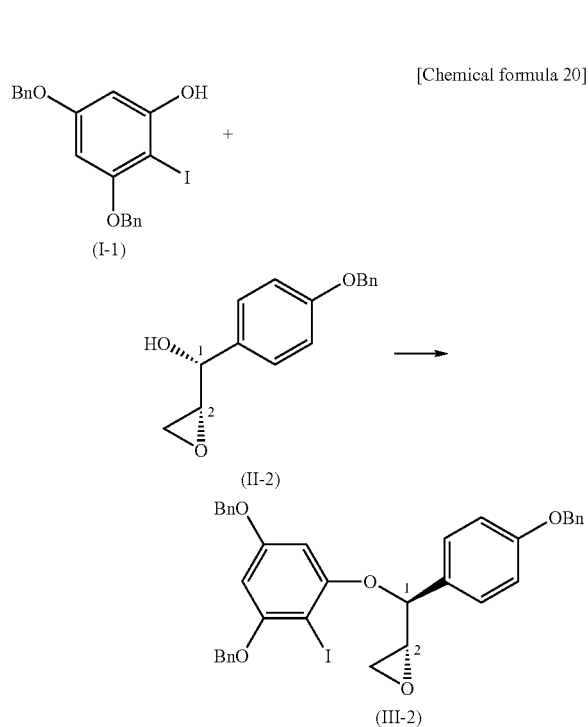

Under argon atmosphere, into a reaction mixture which was prepared by dissolving 20 mg (0.078 mmol) of an alcohol compound (II-2), 40 mg (0.23 mmol) of N,N,N',N'-tetramethyl azodicarboxamide, and 52 mg (0.12 mmol) of a phenol compound (I-1) into 0.80 mL of toluene and then cooled down to 0° C., 0.24 mL (1.0 M, 0.24 mmol) of a toluene solution of tributylphosphine was added dropwise and stirred at 0° C. After one hour, the reaction was quenched by adding water, and the aqueous layer was extracted with ethyl acetate three times. The obtained organic layers were combined, washed with a saturated saline solution, dried over anhydrous magnesium sulfate, and filtered. Then, the solvent was removed by evaporation under reduced pressure. The residue was purified by preparative thin-layer chromatography (n-hexane:toluene:ethyl acetate=4:6:1). Consequently, 38 mg (yield 71%, including diastereomers) of an epoxide (III-2) was obtained as a colorless viscous material.

$^1$H NMR (main diastereomer, 400 MHz, CDCl$_3$) δ 2.82 (dd, 1H, J=7.2, 5.6 Hz), 3.12 (dd, 1H, J=7.2, 3.6 Hz), 3.27-3.31 (m, 1H), 4.85 (s, 2H), 5.03 (s, 2H), 5.05 (s, 1H), 5.15 (d, 1H, J=4.4 Hz), 6.05 (d, 1H, J=3.2 Hz) 6.18 (d, 1H, J=3.2 Hz), 6.92-7.00 (m, 2H), 7.18-7.61 (m, 17H);

IR (neat) 3050, 3010, 2900, 1950, 1870, 1800, 1570, 1500, 1450, 1420, 1370, 1220, 1160, 1100, 1015 cm$^{-1}$;

Elementary Analysis

Calculated (C$_{36}$H$_{31}$IO$_5$): C, 64.48; H, 4.66.

Found: C, 64.28; H, 4.93.

Synthesis of an Iodine-Containing Compound (VI-2a) Having a Free Hydroxyl Group

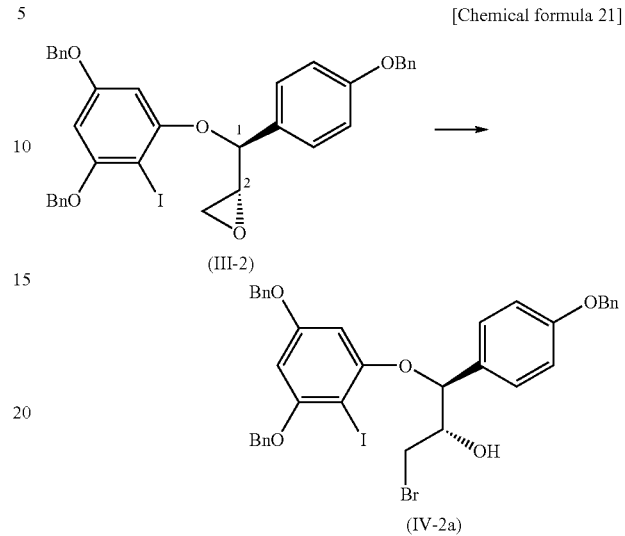

Under argon atmosphere, into a reaction mixture which was prepared by dissolving 21 mg (0.031 mmol) of the epoxide (III-2) into 1.0 mL of tetrahydrofuran and then cooled down to 0° C., 0.12 mL (0.024 mmol) of a tetrahydrofuran solution of Li$_2$NiBr$_4$ was added dropwise and stirred at 0° C. After 12 hours, 0.12 mL (0.024 mmol) of a tetrahydrofuran solution of Li$_2$NiBr$_4$ was again added dropwise thereinto and stirred at 0° C. for 4 hours. Thereafter, 0.04 mL (0.008 mmol) of a tetrahydrofuran solution of Li$_2$NiBr$_4$ was further added dropwise thereinto and stirred at 0° C. for 24 hours. To the reaction solution, a phosphate buffer was added to quench the reaction, and the aqueous layer was extracted with dichloromethane three times. The obtained organic layers were combined, washed with a saturated saline solution, dried over anhydrous magnesium sulfide, and filtered. Then the solvent was removed by evaporation under reduced pressure. The residue was purified by preparative thin-layer chromatography (n-hexane:toluene:ethyl acetate=4:6:1). Consequently, 21 mg (yield 91%) of an iodine-containing compound (VI-2a) having a free hydroxyl group was obtained as a white solid.

$^1$H NMR (400 MHz, CDCl$_3$) δ 2.41 (d, 1H, J=6.6 Hz), 3.65 (dd, 1H, J=10.4, 4.0 Hz), 3.70 (dd, 1H, J=10.4, 6.8 Hz), 4.12-4.17 (m, 1H), 4.80 (d, 1H, J=12.0 Hz), 4.84 (d, 1H, J=12.0 Hz), 5.03 (s, 2H), 5.05 (s, 1H), 5.16 (d, 1H, J=5.6 Hz), 5.99 (d, 1H, J=2.4 Hz), 6.18 (d, 1H, J=2.4 Hz), 6.95 (m, 2H), 7.23-7.55 (m, 17H);

IR (neat) 3567, 3064, 2914, 1951, 1875, 1800, 1575, 1510, 1450, 1425, 1370, 1325 cm$^{-1}$;

$[\alpha]_D^{23}$ −41.5 (c 1.02, CHCl$_3$);

Elementary Analysis

Calculated (C$_{36}$H$_{32}$BrIO$_5$): C, 57.54; H, 4.29.

Found: C, 57.78; H, 4.01.

Synthesis of an Iodine-Containing Compound (VI-2b) Having TBS Ether

Synthesis of a Benzyl and TBS Protected Form (V-2a) of (−)-Afzelechin

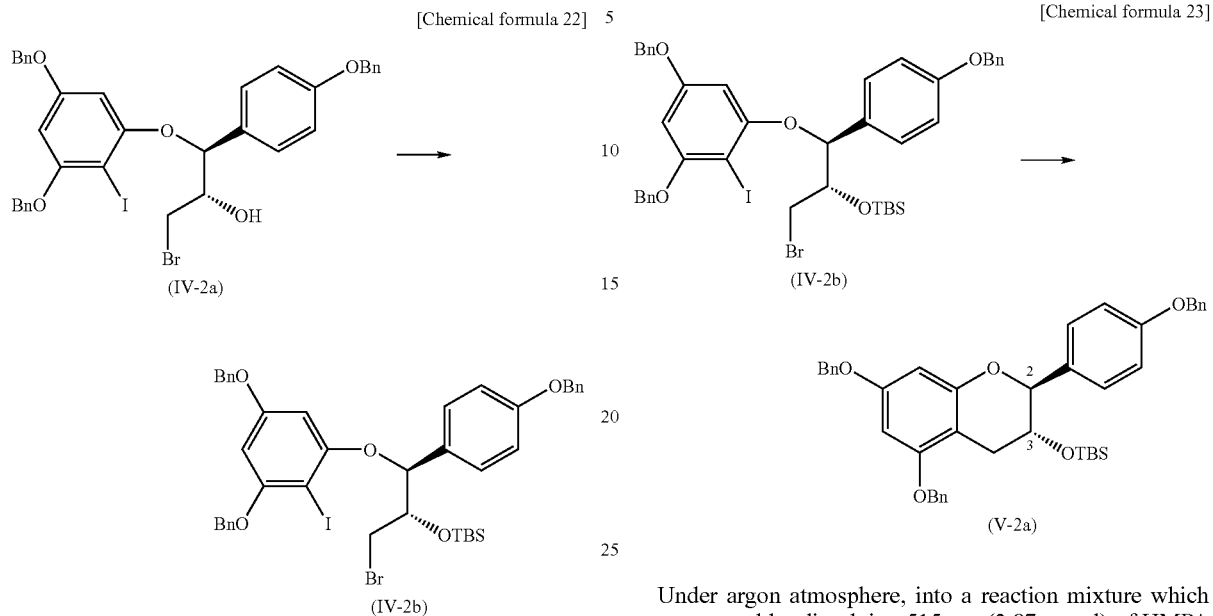

[Chemical formula 22]

[Chemical formula 23]

Under argon atmosphere, into a reaction mixture which was prepared by dissolving 426 mg (0.566 mmol) of the iodine-containing compound (VI-2a) having a free hydroxyl group and 220 mg (2.05 mmol) of 2,6-di-tert-butylpyridine into 10.0 mL of dichloromethane and cooled down to 0° C., 240 mg (0.908 mmol) of tert-butyldimethylsilyl triflate was added dropwise and stirred at 0° C. for 3 hours. Thereafter, 75 mg (0.70 mmol) of 2,6-di-tert-butylpyridine was again added thereto and cooled down to 0° C. Into the reaction mixture, 96.0 mg (0.363 mmol) of tert-butyldimethylsilyl triflate was added dropwise and stirred at 0° C. for 1 hour. After the reaction was quenched by adding a sodium carbohydrate solution, the aqueous layer was extracted with ethyl acetate three times. The obtained organic layers were combined and washed with a saturated saline solution, dried over anhydrous sodium sulfate, and filtered. Then, the solvent was removed by evaporation under reduced pressure. The residue was purified by silica gel chromatography (n-hexane:ethyl acetate=15:1). Consequently, 393 mg (yield 80%) of silyl ether (VI-2b) was obtained as a colorless viscous material.

$^1$H NMR (400 MHz, CDCl$_3$) δ −0.44 (s, 3H), −0.12 (s, 3H), 0.73 (s, 9H), 2.31 (dd, J=16.4, 9.2 Hz), 3.12 (dd, 1H, J=16.4, 5.6 Hz), 3.91-3.97 (m, 1H), 4.61 (d, 1H, J=8.8 Hz), 4.96 (s, 2H) 5.05 (s, 2H), 5.09 (s, 2H), 6.20 (d, 1H, J=2.4 Hz), 6.23 (d, 1H, J=2.4 Hz), 6.96 (m, 1H), 7.21-7.50 (m, 17H);

IR (neat) 2930, 2850, 1575, 1500, 1450, 1420, 1245, 1220, 1160, 1110 cm$^{-1}$;

$[α]_D^{23}$ −52.8 (c 1.37, CHCl$_3$);

Elementary Analysis

Calculated (C$_{42}$H$_{46}$BrIO$_5$Si): C, 58.27; H, 5.36.

Found: C, 58.19; H, 5.60.

Under argon atmosphere, into a reaction mixture which was prepared by dissolving 515 mg (2.87 mmol) of HMPA and 1.52 mL (1.46 mmol) of phenylmagnesium bromide into 1.0 mL of tetrahydrofuran and cooled down to 0° C., 1.28 mL (1.46 mmol) of phenyllithium was added dropwise and stirred at 0° C. for 30 minutes. The reaction mixture was cooled down to −78° C. Into the reaction mixture, tetrahydrofuran solution (0.5 mL) containing 253 mg (0.292 mmol) of the silyl ether (VI-2b) was added dropwise, and stirred at −78° C. for 1 hour. The temperature of the reaction mixture was raised to 0° C., and then further stirred for 10 minutes. Thereafter, the reaction was quenched by adding methanol-D (CH$_3$OD), and an ammonium chloride solution was added thereto. The aqueous layer was extracted with n-hexane three times. The obtained organic layers were combined, washed with a saturated saline solution, dried over anhydrous magnesium sulfate, and filtered. Then, the solvent was removed by evaporation under reduced pressure. The residue was partially purified by silica gel chromatography (n-hexane:toluene:ethyl acetate=32:32:1). Consequently, 122 mg (yield 63%) of a pure benzyl and TBS protected form (V-2a) of afzelechin was obtained as a colorless viscous material. Furthermore, a fraction containing the target substance as a principal component was purified by preparative thin-layer chromatography (n-hexane:toluene:ethyl acetate=16:16:1). Consequently, 62 mg (yield 32%) of a benzyl and TBS protected form (V-2a) of (−)-afzelechin was obtained (total yield 184 mg, 96%).

$^1$H NMR (400 MHz, CDCl$_3$) δ −0.44 (s, 3H), 0.12 (s, 3H), 0.73 (s, 9H), 2.64 (dd, 1H, J=16.4, 9.6 Hz), 3.12 (dd, 1H, J=16.4, 6.0 Hz), 3.90-3.97 (m, 1H), 4.61 (d, 1H, J=8.8 Hz) 4.96 (s, 2H), 5.05 (s, 2H), 5.09 (s, 2H), 6.20 (d, 1H, J=2.0 Hz), 6.23 (d, 1H, J=2.0 Hz), 6.96 (m, 2H), 7.22-7.43 (m, 17H);

IR (neat) 3150, 3050, 2910, 2840, 1940, 1870, 1800, 1610, 1585, 1500, 1490, 1445, 1370, 1240, 1140, 1120, 1140, 1120 cm$^{-1}$;

$[α]_D^{23}$ −35.1 (c 1.08, CHCl$_3$)

Elementary Analysis

Calculated (C$_{42}$H$_{46}$O$_5$Si): C, 76.56; H, 7.04.

Found: C, 76.69; H, 7.14.

Synthesis of a Benzyl Protected Form (V-2b) of (−)-Afzelechin

Synthesis of (−)-Afzelechin (V-2c)

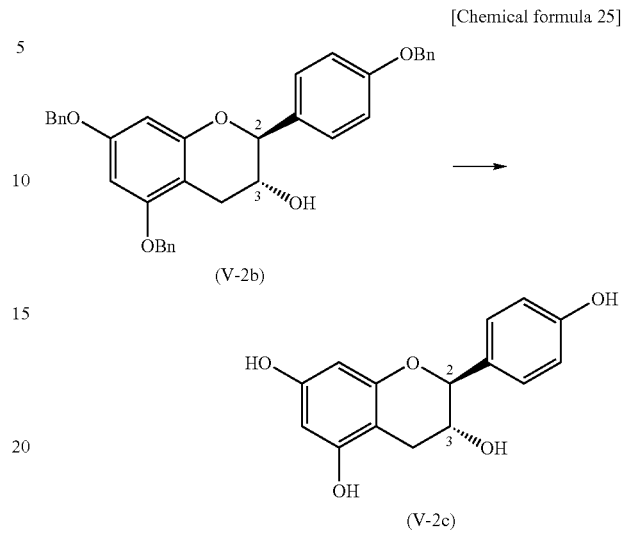

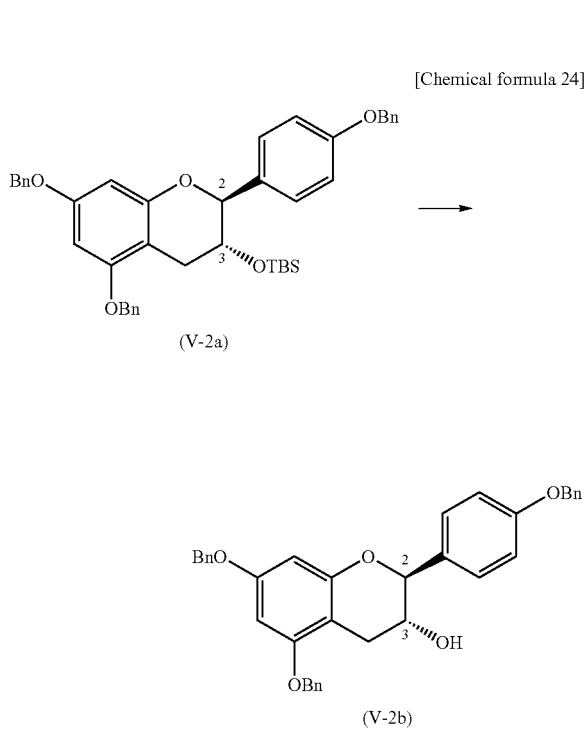

55 mg (0.10 mmol) of a benzyl protected form (V-2b) of (−)-afzelechin was dissolved into 6.9 mL of tetrahydrofuran and 6.9 mL of methanol, and 82 mg of 20% palladium hydroxide was added thereto and stirred at room temperature under hydrogen atmosphere. After 1 hour, under argon gas atmosphere, the mixture was filtrated through a celite pad, and then the filtrate was treated by gel filtration column chromatography Sephadex (trademark) LH-20 (eluate:methanol). The obtained solution of a target substance was concentrated under reduced pressure, and 27 mg (yield 98%) of (−)-afzelechin (V-2c) was obtained as a colorless viscous material.

$^1$H NMR (400 MHz, CD$_3$COCD$_3$) δ 2.53 (dd, 1H, J=16.4, 8.4 Hz), 2.94 (dd, 1H, J=16.4, 5.2 Hz), 3.95 (d, 1H, J=4.8 Hz), 3.97-4.04 (m, 1H), 4.59 (d, 1H, J=8.0 Hz), 5.87 (d, 1H, J=2.0 Hz), 6.02 (d, 1H, J=2.0 Hz), 6.79-6.83 (m, 2H), 7.23-7.26 (m, 2H), 8.20 (br, 4H);

IR (neat) 3320, 1690, 1610, 1510, 1510, 1460, 1600, 1230, 1140, cm$^{-1}$;

$[α]_D^{25}$ −16.8 (c 1.19, acetone);

Elementary Analysis

Calculated (C$_{15}$H$_{14}$O$_5$): C, 65.69; H, 5.15.

Found: C, 65.47; H, 5.30.

Under argon atmosphere, into a reaction mixture which was prepared by dissolving 119 mg (0.180 mmol) of the benzyl and TBS protected form (V-2a) of (−)-afzelechin into 1.0 mL of tetrahydrofuran and then cooled down to 0° C., 0.023 mL (0.23 mmol) of tetrabutylammonium fluoride was added dropwise and stirred at 0° C. for 7 hours. To the reaction mixture, a phosphate buffer was added to quench the reaction, and the aqueous layer was extracted with ethyl acetate three times. The obtained organic layers were combined, washed with a saturated saline solution, dried over anhydrous sodium sulfate, and filtered. The solvent was removed by evaporation under reduced pressure. The residue was purified by preparative thin-layer chromatography (n-hexane:ethyl acetate=3:1). Consequently, 89 mg (yield 90%) of a benzyl protected form (V-2b) of (−)-afzelechin was obtained as a white solid.

$^1$H NMR (400 MHz, CDCl$_3$) δ 1.66 (br, 1H), 2.78 (dd, 1H, J=16.4, 8.8 Hz), 3.11 (dd, 1H, J=16.4, 5.6 Hz), 4.05-4.12 (m, 1H), 4.70 (d, 1H, J=8.4 Hz) 4.99 (s, 2H), 5.03 (m, 2H), 5.09 (s, 2H), 6.22 (d, 1H, J=1.6 Hz), 6.27 (d, 1H, J=1.6 Hz) 7.01-7.03 (m, 2H), 7.30-7.44 (m, 17H);

IR (neat) 3380, 3150, 3010, 2900, 1950, 1870, 1800, 1610, 1580, 1510, 1490, 1450, 1445, 1370, 1240, 1150, 1115, 1045 cm$^{-1}$;

$[α]_D^{24}$ −7.16 (c 1.28, CHCl$_3$)

Elementary Analysis

Calculated (C$_{36}$H$_{32}$O$_5$): C, 79.39; H, 5.92.

Found: C, 79.38; H, 6.00.

The invention claimed is:

1. A method for producing flavan derivatives comprising the steps of:

(1) dehydratively condensing a phenol compound expressed by formula (I) and an alcohol compound expressed by formula (II) to obtain an epoxide compound of formula (III),

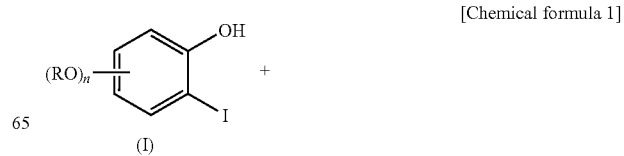

-continued

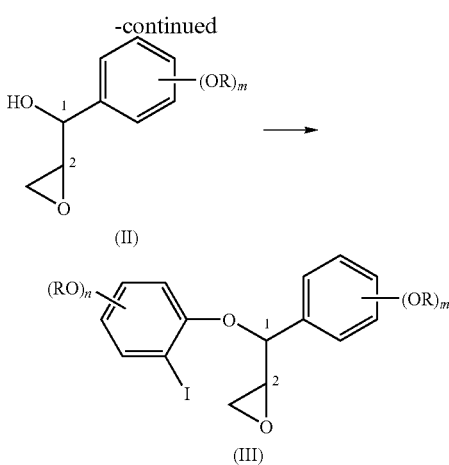

(wherein
R represents, in each of the appearances, H; an allyl group; or an alkyl group, an aryl group or an arylalkyl group, which may be substituted by an alkoxy group, an alkylthio group, an acyloxy group, or an alkoxycarbonyl group;
n represents an integer from 0 to 4; and
m represents an integer from 0 to 5);
(2) opening the epoxy ring of the epoxide compound of formula (III) to obtain an iodine-containing compound of formula (IV),

[Chemical formula 2]

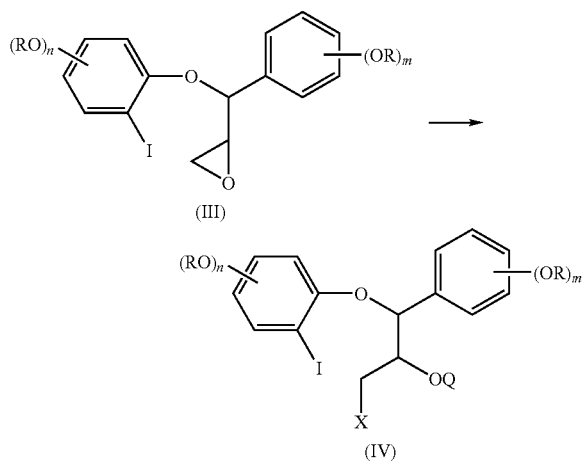

(wherein
R represents, in each of the appearances, H; an allyl group; or any one of an alkyl group, an aryl group or an arylalkyl group which may be substituted by an alkoxy group, an alkylthio group, an acyloxy group, or an alkoxycarbonyl group;
n represents an integer from 0 to 4;
m represents an integer from 0 to 5;
X represents a halogen, an alkylsulfonyloxy group, or an arylsulfonyloxy group; and Q represents H; a silyl group; or an alkyl group, an aryl group or an arylalkyl group which may be substituted by an alkoxy group, an alkylthio group, an acyloxy group or an alkoxycarbonyl group);
(3) cyclizing the iodine-containing compound of formula (IV) to obtain a flavan derivative of formula (V),

[Chemical formula 3]

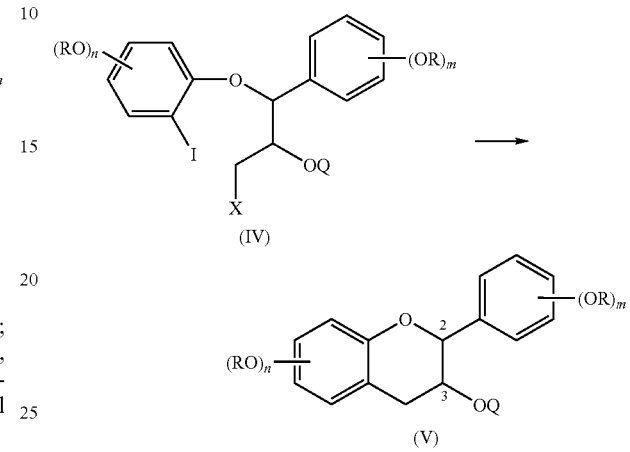

(wherein
R represents, in each of the appearances, H; an allyl group; or an alkyl group, an aryl group or an arylalkyl group which may be substituted by an alkoxy group, an alkylthio group, an acyloxy group or an alkoxycarbonyl group;
n represents an integer from 0 to 4;
m represents an integer from 0 to 5; and
Q represents H; a silyl group, or an alkyl group, an aryl group or an arylalkyl group which may be substituted by an alkoxy group, an alkylthio group, an acyloxy group, or an alkoxycarbonyl group).

2. The method for producing flavan derivatives according to claim 1, wherein the alcohol compound of formula (II) in which the 1-position has (R) configuration is used to obtain the flavan derivative of formula (V) in which the 2-position has (S) configuration.

3. The method for producing flavan derivatives according to claim 1, wherein the alcohol compound of formula (II) in which the 1-position has (S) configuration is used to obtain the flavan derivative of formula (V) in which the 2-position has (R) configuration.

4. The method for producing flavan derivatives according to claim 1, wherein the alcohol compound of formula (II) in which the 2-position has (R) configuration is used to obtain the flavan derivative of formula (V) in which the 3-position has (R) configuration.

5. The method for producing flavan derivatives according to claim 1, wherein the alcohol compound of formula (II) in which the 2-position has (S) configuration is used to obtain the flavan derivative of formula (V) in which the 3-position has (S) configuration.

* * * * *